(12) United States Patent
Alobaid

(10) Patent No.: US 9,283,018 B1
(45) Date of Patent: Mar. 15, 2016

(54) BIODEGRADABLE KYPHOPLASTY BALLOON SYSTEM

(71) Applicant: Abdulrazzaq Alobaid, Kuwait (KW)

(72) Inventor: Abdulrazzaq Alobaid, Kuwait (KW)

( * ) Notice: Subject to any disclaimer, the term of this patent is extended or adjusted under 35 U.S.C. 154(b) by 0 days.

(21) Appl. No.: 14/940,112

(22) Filed: Nov. 12, 2015

(51) Int. Cl.
| | |
|---|---|
| *A61B 17/88* | (2006.01) |
| *A61B 17/70* | (2006.01) |
| *A61B 17/00* | (2006.01) |
| *A61B 17/56* | (2006.01) |
| *A61M 25/00* | (2006.01) |

(52) U.S. Cl.
CPC ......... *A61B 17/8855* (2013.01); *A61B 17/7097* (2013.01); *A61B 17/8852* (2013.01); *A61B 2017/00004* (2013.01); *A61B 2017/00862* (2013.01); *A61B 2017/564* (2013.01); *A61M 2025/0024* (2013.01)

(58) Field of Classification Search
CPC .......... A61B 17/8852; A61B 17/8805; A61M 2025/0024
See application file for complete search history.

(56) References Cited

U.S. PATENT DOCUMENTS

| | | | | |
|---|---|---|---|---|
| 5,100,385 | A * | 3/1992 | Bromander | A61M 25/104 604/913 |
| 6,623,452 | B2 * | 9/2003 | Chien | A61M 25/10 604/101.01 |
| 8,734,459 | B1 | 5/2014 | Alobaid | |
| 8,900,304 | B1 | 12/2014 | Alobaid | |
| 2012/0065694 | A1 | 3/2012 | Simonson | |
| 2012/0165732 | A1* | 6/2012 | Muller | A61B 17/8855 604/99.01 |
| 2013/0325036 | A1 | 12/2013 | Bonutti | |

FOREIGN PATENT DOCUMENTS

| | | |
|---|---|---|
| CN | 103284782 A | 9/2013 |
| JP | 2009-285135 | 12/2009 |

\* cited by examiner

*Primary Examiner* — Andrew Yang
(74) *Attorney, Agent, or Firm* — Richard C. Litman

(57) ABSTRACT

The biodegradable kyphoplasty balloon system includes a biodegradable balloon catheter and a delivery system. The biodegradable balloon catheter includes an elastomeric tube and a biodegradable balloon. The elastomeric tube has opposed open and closed ends with a resealable slit being formed in a central portion thereof. The elastomeric tube is formed from an elastomer such that the resealable slit acts as a one-way inflation valve. The biodegradable balloon is mounted on the elastomeric tube such that the biodegradable balloon is sealed thereto about the resealable slit for selective inflation thereof. The delivery system includes a hollow push tube and an inflation tube. The hollow push tube has opposed first and second open ends. The inflation tube has opposed open and closed ends, with an aperture being formed through the inflation tube adjacent the closed end thereof. The hollow push tube slidably receives the inflation tube.

10 Claims, 3 Drawing Sheets

BIODEGRADABLE KYPHOPLASTY BALLOON SYSTEM

BACKGROUND OF THE INVENTION

1. Field of the Invention

The present invention relates generally to medical spinal procedures, and particularly to a biodegradable kyphoplasty balloon system for performing kyphoplasty on a fractured vertebra.

2. Description of the Related Art

Kyphoplasty is a medical spinal procedure in which bone cement is injected through a small hole in the skin (i.e., percutaneously) into a fractured vertebra with the goal of relieving back pain caused by vertebral compression fractures. Specifically, kyphoplasty is a variation of a vertebroplasty which attempts to restore the height and angle of kyphosis of a fractured vertebra (of certain types), followed by its stabilization using injected bone cement. The procedure typically includes the use of a small balloon that is inflated in the vertebral body to create a void within the cancellous bone prior to cement delivery. In typical kyphoplasty, once the void is created, the procedure continues in a similar manner as a vertebroplasty, but the bone cement is delivered directly into the newly created void.

Due to the direct filling of the vertebral body with the bone cement in conventional kyphoplasty, there are risks of leakage of acrylic cement to outside of the vertebral body. Although severe complications are extremely rare, infection, bleeding, numbness, tingling, headache, and paralysis may ensue because of misplacement of the needle or cement. Thus, a biodegradable kyphoplasty balloon system addressing the aforementioned problems is desired.

SUMMARY OF THE INVENTION

The biodegradable kyphoplasty balloon system includes a biodegradable balloon catheter and a delivery system. The biodegradable balloon catheter includes an elastomeric tube and a biodegradable balloon. The elastomeric tube has opposed open and closed ends with a resealable slit being formed in a central portion thereof. The elastomeric tube is formed from an elastomeric material, such as silicone or the like, such that the resealable slit acts as a one-way inflation valve. The biodegradable balloon is mounted on the elastomeric tube such that the biodegradable balloon is sealed thereto about the resealable slit for selective inflation thereof.

The delivery system includes a hollow push tube and an inflation tube. The hollow push tube has opposed first and second open ends, and the inflation tube has opposed open and closed ends. The hollow push tube slidably receives a central portion of the inflation tube, with an aperture being formed through the inflation tube adjacent the closed end thereof. The elastomeric tube of the biodegradable balloon catheter slidably receives the inflation tube such that the aperture formed through the inflation tube may be selectively aligned with the resealable slit formed in the elastomeric tube for selective inflation of the biodegradable balloon. Preferably, a push handle is mounted on the hollow push tube adjacent the second end thereof and an inflation luer is mounted on the inflation tube adjacent the open end thereof.

In use for a kyphoplasty procedure, the biodegradable balloon catheter is inserted into a vertebral body. The aperture formed through the inflation tube is aligned with the resealable slit formed in the elastomeric tube. Bone cement is then injected through the inflation tube to inflate and fill the biodegradable balloon with the bone cement. The inflation tube may then be removed from the elastomeric tube of the biodegradable balloon catheter. The biodegradable balloon catheter can be maintained in position within the vertebral body by releasable contact with the hollow push tube.

These and other features of the present invention will become readily apparent upon further review of the following specification and drawings.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
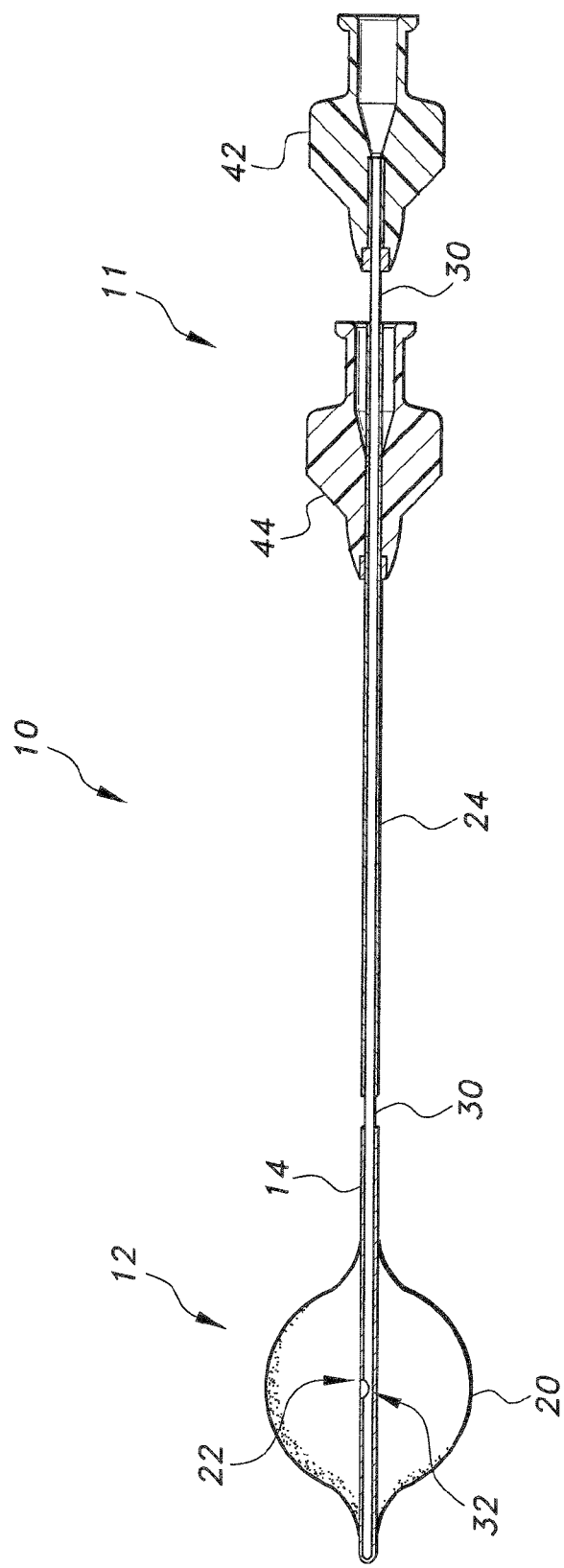
FIG. 1 is a side view of a biodegradable kyphoplasty balloon system according to the present invention.
Figure 2:
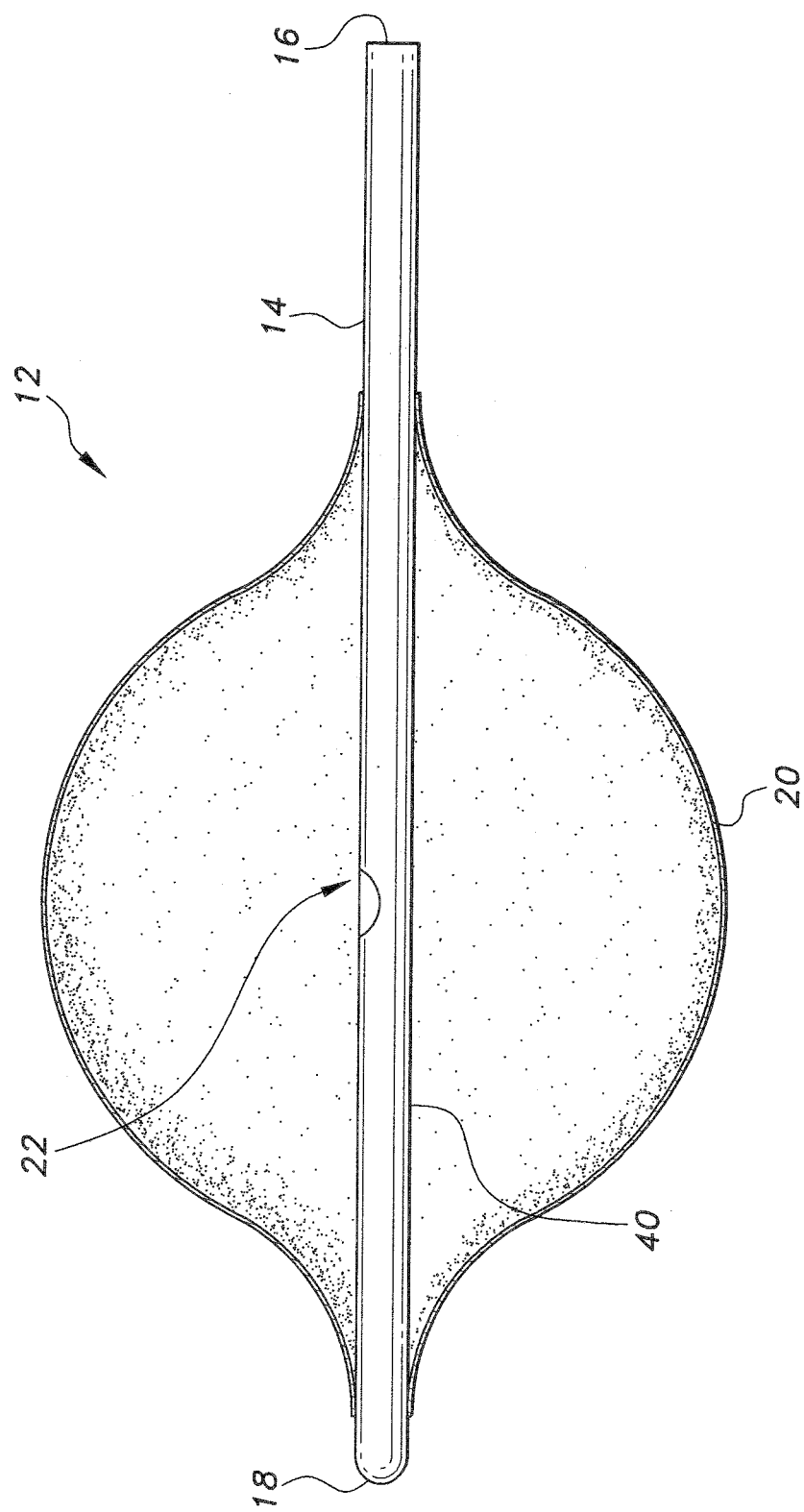
FIG. 2 is a side view of a biodegradable balloon catheter of the biodegradable kyphoplasty balloon system.

Referring now to FIG. 1, the biodegradable kyphoplasty balloon system 10 includes a biodegradable balloon catheter 12 and a delivery system 11. As best shown in FIG. 2, the biodegradable balloon catheter 12 includes an elastomeric tube 14 and a biodegradable balloon 20. The elastomeric tube 14 has opposed open and closed ends 16, 18, respectively, with a resealable slit 22. The resealable slit 22 is preferably formed in a central portion 40 of the elastomeric tube 14. The elastomeric tube 14 is formed from an elastomeric material, such as silicone or the like, such that the resealable slit 22 acts as a one-way inflation valve. The biodegradable balloon 20 is mounted on the elastomeric tube 14 such that the biodegradable balloon 20 is sealed thereto about the resealable slit 22 for selective inflation thereof.

Figure 3:
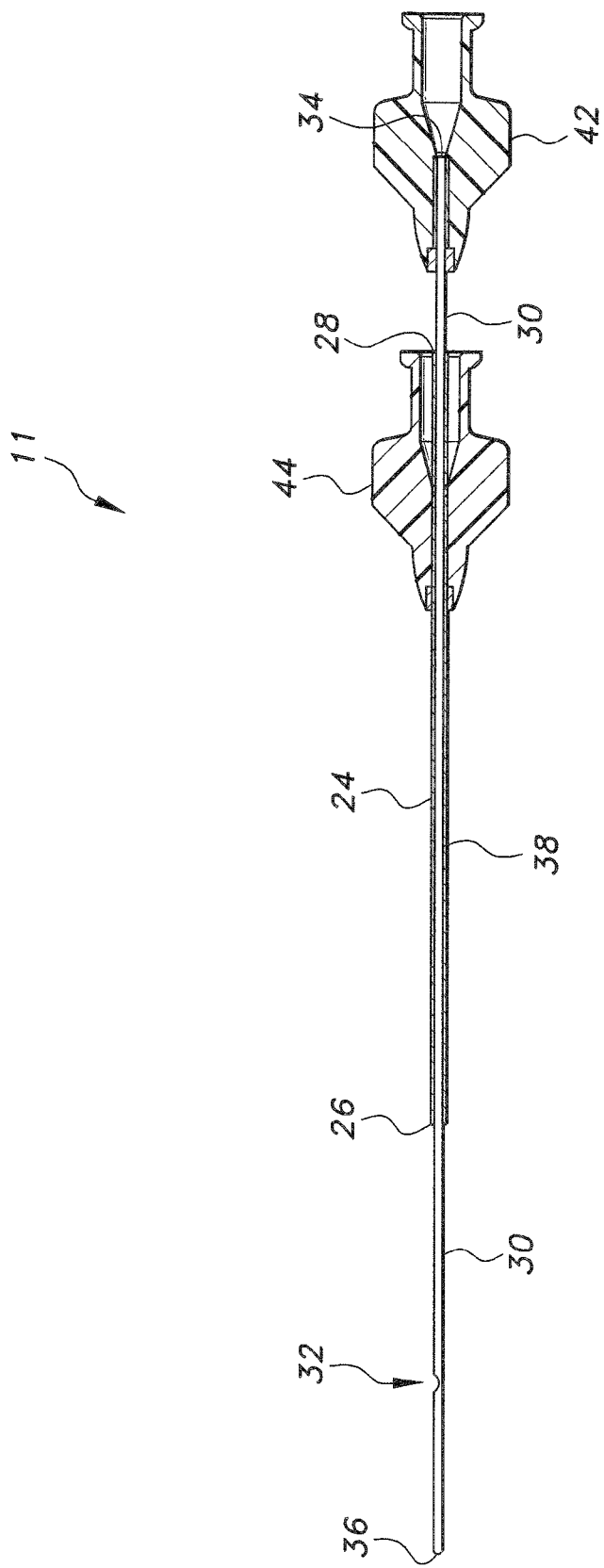
FIG. 3 is a side view of a delivery system of the biodegradable kyphoplasty balloon system.

As best shown in FIG. 3, the delivery system 11 includes a hollow push tube 24 and an inflation tube 30. The hollow push tube 24 has opposed first and second open ends 26, 28, respectively, and the inflation tube 30 has opposed open and closed ends 34, 36, respectively. The hollow push tube 24 slidably receives at least a first portion 38, e.g., a central portion 38, of the inflation tube 30. An aperture 32 is formed through the inflation tube 30, adjacent the closed end 36. The hollow push tube 24 can be releasably attached to the catheter 12 at first end 26 of the hollow push tube 24.

As shown in FIG. 1, the elastomeric tube 14 of the biodegradable balloon catheter 12 slidably receives at least a second portion of the inflation tube 30 such that the aperture 32 formed through the inflation tube 30 may be selectively aligned with the resealable slit 22 formed in the elastomeric tube 14 for selective inflation of the biodegradable balloon 20. Preferably, a push handle 44 is mounted on the hollow push tube 24 adjacent the second end 28, and an inflation luer 42 is mounted on the inflation tube 30 adjacent the open end 34. It should be understood that any suitable type of handle and/or luer may be used, as are well known in the field of catheter delivery systems and the like.

In use for a kyphoplasty procedure, the biodegradable balloon catheter 12 is inserted into a vertebral body, as in a conventional kyphoplasty procedure. The aperture 32 formed through the inflation tube 30 is aligned with the resealable slit 22 formed in the elastomeric tube 14 (as in the configuration shown in FIG. 1). Bone cement is then injected through the inflation tube 30 to inflate and fill the biodegradable balloon 20 with the bone cement, as in conventional kyphoplasty. The inflation tube 30 may then be removed from the elastomeric tube 14 of the biodegradable balloon catheter 12, with the biodegradable balloon catheter 12 being maintained in position within the vertebral body by releasable contact with the hollow push tube 24 while the inflation tube 30 is pulled out using the inflation luer 42. For example, first end 26 of hollow push 24 is held against open end 16 of elastomeric tube 14, holding the biodegradable balloon catheter 12 in place, while the inflation tube 30 is slid out of elastomeric tube 14.

The resealable slit 22 formed in the elastomeric tube 14 acts as a one-way valve, only being open when the bone cement is injected therethrough under pressure, but when the aperture 32 is moved out of alignment therewith, the resealable slit 22 closes, preventing leakage of the bone cement from the biodegradable balloon 20. The biodegradable balloon 20 is formed from a biodegradable material, such that the bone cement remains within the biodegradable balloon within the vertebral body until the biodegradable balloon 20 naturally degrades. It should be understood that any suitable type of biodegradable material may be utilized, including for example, materials having poly (glycolic acid) (PGA), poly (lactic acid) (PLA), and/or copolymers thereof.

It is to be understood that the present invention is not limited to the embodiments described above, but encompasses any and all embodiments within the scope of the following claims.

I claim:

1. A biodegradable kyphoplasty balloon system, comprising:
    a biodegradable balloon catheter comprising:
    an elastomeric tube having opposed open and closed ends, a resealable slit being formed in a central portion of the elastomeric tube; and
    a biodegradable balloon mounted on the elastomeric tube such that the biodegradable balloon is sealed thereto about the resealable slit for selective inflation thereof; and
    an inflation tube having opposed open and closed ends, an aperture being formed through said inflation tube adjacent the closed end thereof,
    wherein the elastomeric tube of said biodegradable balloon catheter slidably receives the inflation tube such that the aperture formed through said inflation tube may be selectively aligned with the resealable slit formed in the elastomeric tube for selective inflation of the biodegradable balloon.

2. The biodegradable kyphoplasty balloon system as recited in claim 1, further comprising a hollow push tube having opposed first and second open ends, the hollow push tube slidably receiving a portion of said inflation tube.

3. The biodegradable kyphoplasty balloon system as recited in claim 2, further comprising a push handle mounted on the hollow push tube adjacent the second end thereof.

4. The biodegradable kyphoplasty balloon system as recited in claim 1, further comprising an inflation luer mounted on the inflation tube adjacent the open end thereof.

5. The biodegradable kyphoplasty balloon system as recited in claim 1, wherein the elastomeric tube is formed from silicone.

6. A biodegradable kyphoplasty balloon system, comprising:
    a biodegradable balloon catheter comprising:
    an elastomeric tube having opposed open and closed ends, a resealable slit being formed in a portion of the elastomeric tube; and
    a biodegradable balloon mounted on the elastomeric tube such that the biodegradable balloon is sealed thereto about the resealable slit for selective inflation thereof;
    a hollow push tube having opposed first and second open ends; and
    an inflation tube having opposed open and closed ends, said hollow push tube slidably receiving at least a portion of said inflation tube, an aperture being formed through said inflation tube,
    wherein the elastomeric tube of said biodegradable balloon catheter slidably receives at least a portion of the inflation tube such that the aperture formed through said inflation tube may be selectively aligned with the resealable slit formed in the elastomeric tube for selective inflation of the biodegradable balloon.

7. The biodegradable kyphoplasty balloon system as recited in claim 6, further comprising a push handle mounted on the hollow push tube adjacent the second end thereof.

8. The biodegradable kyphoplasty balloon system as recited in claim 6, further comprising an inflation luer mounted on the inflation tube adjacent the open end thereof.

9. The biodegradable kyphoplasty balloon system as recited in claim 6, wherein the elastomeric tube is formed from silicone.

10. A method of performing kyphoplasty, comprising the steps of:
    inserting a biodegradable balloon catheter into a vertebral body, the biodegradable balloon catheter having an elastomeric tube having opposed open and closed ends, a resealable slit being formed in a portion of the elastomeric tube, and a biodegradable balloon mounted on the elastomeric tube such that the biodegradable balloon is sealed thereto about the resealable slit;
    providing a hollow push tube having opposed first and second open ends;
    providing an inflation tube having opposed open and closed ends, said hollow push tube slidably receiving at least a portion of said inflation tube, an aperture being formed through said inflation tube;
    aligning the aperture formed through the inflation tube with the resealable slit formed in the elastomeric tube;
    injecting bone cement through the inflation tube to inflate and fill the biodegradable balloon with the bone cement; and
    removing the inflation tube from the elastomeric tube of the biodegradable balloon catheter, the biodegradable balloon catheter being maintained in position within the vertebral body by releasable contact with the hollow push tube.

* * * * *